(12) United States Patent
Tan et al.

(10) Patent No.: US 11,548,846 B2
(45) Date of Patent: Jan. 10, 2023

(54) METHOD OF PREPARING 8-METHYLDECANAL

(71) Applicant: Panasia (Wuhan) Food Science Technology Co., Ltd, Ezhou (CN)

(72) Inventors: Yafei Tan, Ezhou (CN); Xinhao Dong, Ezhou (CN); Hua Zheng, Ezhou (CN); Guotai Lei, Ezhou (CN); Xiaoli Zhu, Ezhou (CN)

( * ) Notice: Subject to any disclaimer, the term of this patent is extended or adjusted under 35 U.S.C. 154(b) by 0 days.

(21) Appl. No.: 17/647,015

(22) Filed: Jan. 5, 2022

(65) Prior Publication Data
US 2022/0127214 A1   Apr. 28, 2022

(30) Foreign Application Priority Data
Sep. 7, 2021   (CN) .......................... 202111044733.1

(51) Int. Cl.
*C07C 45/29*   (2006.01)
*C07C 29/00*   (2006.01)

(52) U.S. Cl.
CPC .................... *C07C 45/29* (2013.01)

(58) Field of Classification Search
CPC ....... C07C 45/29; C07C 45/30; C07C 29/103; C07C 29/129
See application file for complete search history.

(56) References Cited

U.S. PATENT DOCUMENTS

| 2013/0253076 A1 | 9/2013 | Joichi et al. |
| 2014/0315772 A1 | 10/2014 | Cunningham |
| 2016/0207862 A1 | 7/2016 | Hojo |

*Primary Examiner* — Sikarl A Witherspoon
(74) *Attorney, Agent, or Firm* — Rumit Ranjit Kanakia

(57) ABSTRACT

The present invention discloses a novel method of preparing 8-methyldecanal, a flavor and fragrance material. Specifically, starting from cheap and readily available material 6-chloro-1-hexanol, first, the hydroxyl group was protected with dihydropyran catalyzed by para-toluene sulfonic acid to produce 6-chloro-hexyl tetrahydropyran ether. Then 6-chloro-hexyl tetrahydropyran ether reacted with magnesium turnings to form a Grignard reagent and reacted with 1-bromo-2-methyl-butane under the catalysis of cuprous bromide to give the intermediate 8-methyl-sunny tetrahydropyran ether. Without purification, crude 8-methyl-sunny tetrahydropyran ether was treated under acidic conditions to remove the protecting group to generate 8-methyl-1-decyl alcohol. Finally, 8-methyl decanal was obtained after oxidation with 2, 2, 6, 6-tetramethylpiperidinyloxy. The novel method of preparing 8-methyldecanal disclosed in the present invention utilizes common raw materials with low costs, the reaction conditions are mild, and yield is high. It is suitable for large-scale production.

10 Claims, 1 Drawing Sheet

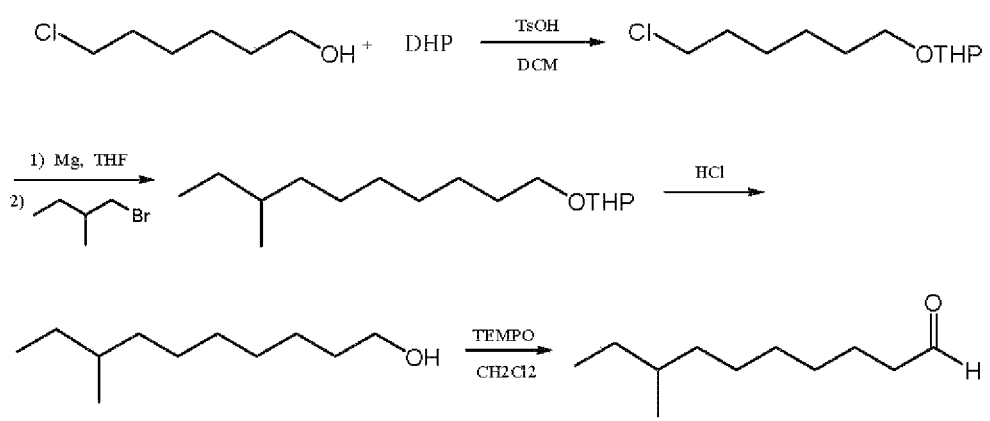

METHOD OF PREPARING 8-METHYLDECANAL

FIELD OF THE INVENTION

The present invention belongs to the technical field of chemical synthesis, it discloses a novel method of preparing 8-methyldecanal.

BACKGROUND OF THE INVENTION 8-methyldecanal (CAS #127793-88-8) exists naturally in citrus fruits. USA and the European Union have approved the use of 8-methyldecanal in food flavors (FEMA #4795). 8-Methyldecanal is a valuable flavor material, it is widely used in the manufacturing of citrus flavors, fruit flavors, confectionary flavors, and other food additives.

EP0448740 discloses the following method of preparing 8-methyldecanal:
In the process, intermediate ethyl 8-methyl-6-decanoate is prepared by Wittig reaction of ethyl 6-bromocaproate with 2-methyl butyraldehyde in the presence of triphenylphosphine and a strong base such as sodium hydride. Then ethyl 8-methyl-6-decanoate is reduced by lithium aluminum hydride to provide 8-methyl-6-decene-1-ol; catalytic hydrogenation of the unsaturated alcohol gives saturated alcohol 8-methyl-1-decyl alcohol. In the last step, oxidation by pyridine chlorochromate (PCC) generates 8-methyldecanal. In this process, flammable and potentially explosive organic metallic reagents (sodium hydride and lithium aluminum hydride) are used; the reaction conditions have to be anhydrous and oxygen-free. In addition, the starting material of ethyl 6-bromocaproate is expensive, and the by-products triphenylphosphonium oxide and chromium salt are not environmental friendly. As a result, this process is not suitable for large-scale production.

JP2008100960 discloses the following synthesis method of 8-methyldecanal:
Starting material 1-bromo-2-methyl butane reacts with magnesium turnings to form a Grignard reagent and then reacts with 6-bromo-hexonitrile in the presence of cuprous bromide and organic base N-methyl pyrrolidone to provide the intermediate 8-methyl-decanitrile. 8-methyl-decanitrile is then reduced by diisobutyl aluminum hydride (DIBAL) and worked up under acidic conditions to give 8-methyldecanal. Although the reaction sequence of this process is relatively short, the starting material 1-bromo-2-methyl butane is expensive, the preparation of 6-bromo-hexonitrile requires highly toxic cyanide raw material, and the reduction with diisobutyl aluminum hydride needs to be carried out at a low temperature of −60° C. As a result, this process is not suitable for large-scale production.

Currently, the application of 8-methyldecanal is largely hampered by its availability. A new process of preparing 8-methyldecanal, which is environmental friendly and cost effective is needed.

SUMMARY OF THE INVENTION

The present invention discloses a novel method of preparing 8-methyldecanal. This novel process avoids the problems in the existing process, such as expensive starting materials, toxic by-products, and harsh reaction conditions etc.

The novel method of preparing 8-methyldecanal comprises the following steps:

S1 Protection of the hydroxyl group of 6-chloro-1-hexanol: 6-chloro-1-hexanol dihydropyran (DHP) were reacted in the presence of an acidic catalyst para-toluenesulfonic acid (TsOH), to produce 6-chloro-hexyl tetrahydropyran ether.

S2 Preparation of 8-methyl-decyl tetrahydropyran ether: the 6-chloro-hexyl tetrahydropyran ether obtained in step S1 reacted with magnesium turnings to form a Grignard reagent and then reacted with 1-bromo-2-methyl-butane to form 8-methyl-decyl-tetrahydropyran ether.

S3 Deprotection of 8-methyl-decyl-tetrahydropyran ether: under acidic conditions, 8-methyl-decyl tetrahydropyran ether obtained in step S2 was de-protected to give 8-methyldecanol.

S4 Preparation of 8-methyldecanal: the 8-methyldecanol obtained in step S3 was oxidized with 2, 2, 6, 6-tetramethylpiperidinyloxy (TEMPO) to generate the product 8-methyldecanal.

Further, in step S1, the method for protecting the hydroxyl group of 6-chloro-1-hexanol is as follows: p-toluenesulfonic acid and 6-chloro-1-hexanol were mixed in dichloromethane, the temperature was kept between 0-10° C., under nitrogen atmosphere, dihydropyran was added dropwise. After the addition, the reaction mixture was stirred for 1-2 h. Then the mixture was neutralized with a small amount of saturated sodium bicarbonate solution. The organic phase was separated, washed, dried, filtered, concentrated, and distilled under vacuum. After distillation, 6-chloro-hexyl tetrahydropyran ether intermediate was obtained.

Furthermore, the molar ratio of the amount of p-toluenesulfonic acid, 6-chloro-1-hexanol, and dihydropyran are (0.05-0.15):1:(1-2).

Furthermore, the volume of dichloromethane used is 4-6 times the volume of 6-chloro-1-hexanol.

Furthermore, in step S2, the synthesis of 8-methyl-decyl tetrahydropyran ether is as follows: magnesium turnings was stirred in tetrahydrofuran, under nitrogen atmosphere, iodine and 1,2-dibromoethane were added, then 6-chloro-hexyl tetrahydropyran ether was added dropwise, the reaction temperature was kept below 60° C. After the addition was complete, the reaction mixture was stirred for 2-3 h. Cuprous bromide was added when the temperature was lowered to 35-45° C., then 1-bromo-2-methyl-butane was added dropwise. After the addition, the reaction was continued for 5-8 h. Saturated ammonium chloride solution was added, and the mixture was extracted with an organic solvent. Then the organic phase was washed, dried, filtered, and concentrated to produce crude 8-methyldecyl tetrahydropyran ether.

Furthermore, the molar ratio of magnesium, 1,2-dibromoethane, 6-chloro-hexyl tetrahydropyran ether, cuprous bromide, and 1-bromo-2-methyl-butane is (1.2-1.5):(0.1-0.2):1:(0.1-0.2):(1.5-2), the amount of iodine added is 0.03 to 0.08 times the amount of 6-chloro-hexyl tetrahydropyran ether, the volume of tetrahydrofuran is 4-6 times of that of 6-chloro-hexyl tetrahydropyran ether, the volume of other organic solvents consumed is 8-12 times of that of 6-chloro-hexyl tetrahydropyran ether.

Furthermore, in step S3, the deprotection of 8-methyl-decyl tetrahydropyran ether is as follows: crude 8-methyl decyl tetrahydropyran ether was dissolved in methanol, then excessive of acid solution was added slowly, the reaction temperature was kept below 40° C. After the reaction was complete, the pH was adjusted to neutral, brine was added. An organic solvent was used to extract the reaction mixture, then the organic phase was separated, washed, dried, filtered, concentrated, and distilled under vacuum to provide 8-methyldecanol.

Furthermore, the volume of methanol used is 4-6 times of the volume of 8-methyldecyl tetrahydropyran ether, the volume of other organic solvent used is 4-6 times of the volume of 8-methyldecyl tetrahydropyran ether. The acid could be hydrochloric acid, sulfuric acid, acetic acid, and nitric acid.

Furthermore, in step S4, the synthesis of 8-methyldecanal is as follows: 2, 2, 6, 6-tetramethylpiperidinyloxy, tetrabutylammonium hydrogen sulfate, and sodium hypochlorite were added to the mixture of dichloromethane and water, the temperature of the reaction mixture was kept between 3-8° C., then 8-methyldecanol was added dropwise. After the addition was complete, the reaction was stirred for 1 h, then saturated sodium sulfite solution was added. Organic phase was separated, and aqueous phase was extracted with an organic solvent. The combined organic phase was washed, dried, filtered, concentrated, and distilled under vacuum to obtain 8-methyldecanal.

Furthermore, the molar ratio of 2, 2, 6, 6-tetramethylpiperidinyloxy, tetrabutylammonium hydrogen sulfate, sodium hypochlorite, and 8-methyldecanol is (0.08-0.12):(0.02-0.08):(1.0-1.5):1, the volume ratio of the dichloromethane and the water is (4-6):1, the volume of the dichloromethane used is 4-6 times of the volume of 8-methyldecanol, the volume of other organic solvent used is 2-3 times of that of 8-methyldecanol.

The method disclosed in this invention uses 6-chloro-1-hexanol as starting material, through hydroxyl protection of 6-chloro-1-hexanol, the preparation of 8-methyl-decyl tetrahydropyran ether, and deprotection of 8-methyl-decyl tetrahydropyran ether to produce 8-methyldecanol, finally, 8-methyl decanal is prepared after oxidation.

This is a new 8-methyldeanal synthesis method, the starting materials are easily available, and the yield is high. The new method is suitable for large-scale industrial production.

Compared with the prior art, the new method has the following advantages:

The new synthesis process uses cheap and readily available raw materials such as 6-chloro-1-hexanol. Firstly, the hydroxyl group of 6-chloro-1-hexanol was protected by reaction with dihydropyran to obtain 6-chloro-hexyl tetrahydropyran ether, then 6-chloro-hexyl tetrahydropyran ether reacted with magnesium turnings to form a Grignard reagent and reacted with 1-bromo-2-methyl-butane under cuprous bromide catalysis to produce the intermediate 8-methyl-decyl tetrahydropyran ether. The intermediate was used without purification and was deprotected under acidic conditions to obtain 8-methyldecanol. Finally, the product 8-methyl decanal is obtained after oxidation with 2, 2, 6, 6-tetramethylpiperidinyloxy. The new synthesis process uses cheap and readily available raw materials, reaction conditions are mild, and yield is high. It is suitable for large-scale industrial production, and has a bright application prospect in the field of food additives.

BRIEF DESCRIPTION OF THE DRAWINGS

FIG. 1 is a flowchart of the preparation process of the 8-methyl decanal of the present invention.

DETAILED DESCRIPTION OF THE INVENTION

The technical proposal of the invention will be clearly and completely described in combination with specific embodiments. The described embodiments are only some embodiments of the present invention but not all embodiments. Based on the embodiment of the invention, all other embodiments obtained by ordinary technicians in the field without creative work fall within the scope of the protection of the invention.

The raw materials and equipment used in the invention, unless specified, are purchased from commercial suppliers.

The invention provides a method of preparing 8-methyl decanal, which comprises the following steps:

S1 Hydroxyl group protection of 6-chloro-1-hexanol: in the presence of p-toluenesulfonic acid, 6-chloro-1-hexanol reacted with dihydropyran to give 6-chloro-hexyl tetrahydropyran ether.

S2 Preparation of 8-methyl-decyl tetrahydropyran ether: The 6-chloro-hexyl tetrahydropyran ether obtained in step S1 reacted with magnesium turnings to form a Grignard reagent. Under the catalyst of cuprous bromide, the Grignard reagent reacted with 1-bromo-2-methyl-butane to obtain the intermediate 8-methyl-decyl tetrahydropyran ether:

S3 Deprotection of 8-methyl-decyl tetrahydropyran ether: under acidic conditions, 8-methyl-decyl tetrahydropyran ether obtained in step S2 was deprotected to afford 8-methyldecanol:

S4 Preparation of 8-methyldecanal: 8-methyldecanol obtained from step S3 was oxidized with 2, 2, 6, 6-tetramethylpiperidinyloxy to afford the product 8-methyldecanal.

Example 1

The example discloses a novel method of preparing 8-methyl decanal, which comprises the following steps:

S1 Protection of the hydroxyl group of 6-chloro-1-hexanol: 80 mL of dichloromethane was added to a three-neck flask equipped with a stirrer, a dropping funnel and a thermometer. 0.086 g of p-toluenesulfonic acid and 16.44 g of 6-chloro-1-hexanol were added to the flask under nitrogen and the temperature of the reaction system was kept between 0-10° C. Then 8.4 g of 3, 4-dihydropyran was added through the dropping funnel. The reaction was exothermic, the temperature of the reaction system was kept between 0-10° C. by adjusting the addition rate. After the addition was complete, the reaction was continued at low temperature for 1-2 h, then 40 mL of saturated sodium bicarbonate solution was added. The mixture was stirred for 10-15 min, 20 mL of water was added. The organic phase was separated, washed with saturated sodium chloride solution, dried with anhydrous sodium sulfate, filtered, and concentrated to obtain 24.56 g of crude product.

After short-range vacuum distillation, 24.33 g of 6-chloro-hexyl tetrahydropyran ether was obtained, b.p. 145° C./0.16 mmHg, with a yield of 91.8%.

S2 Preparation of 8-methyl-decyl tetrahydropyran ether: 80 mL of anhydrous tetrahydrofuran was added to a three-neck flask equipped with a stirrer, a dropping funnel and a thermometer. Under nitrogen atmosphere, 3.6 g of magnesium turnings, 0.6 g of iodine, and 1.32 g of 1, 2-dibromo-ethane were added to the flask. The reaction temperature was kept below 60° C., and 17.66 g of 6-chloro-1-hexanol tetrahydropyran ether was added dropwise. Because the reaction was exothermic, the reaction temperature was kept below 60° C. by adjusting the addition rate. After the addition was complete, the reaction mixture was gently refluxed for 2 hours, while the solution changed from yellow color to clear and to black, and most of the magnesium turnings disappeared. Then system temperature was lowered to 35-45° C., 0.286 g of cuprous bromide was added in one portion. 7.55 g of 1-bromo-2-methyl-butane was added dropwise. After addition was complete, the reaction system was heated to gently refluxing, and continued refluxing for 5-8 h. Afterwards, the mixture was cooled down to room temperature, 200 mL of saturated ammonium chloride solution, and 200 mL of ethyl acetate were added to the mixture. The organic phase was separated, washed with brine, dried with anhydrous sodium sulfate, filtered, and concentrated. 18.6 g of crude 8-methyl decyl tetrahydropyran ether was obtained. The crude product does not need to be purified and can be directly used in the next hydroxyl deprotection step.

S3 Deprotection of 8-methyl-decyl tetrahydropyran ether: 80 mL of methanol was added to a three-neck flask equipped with a stirrer, a dropping funnel, and a thermometer. 18.6 g of crude 8-methyl decyl tetrahydropyran ether was added, then 40 mL of 2M hydrochloric acid solution was added dropwise. Because the reaction was exothermic, the reaction temperature was kept below 40° C. by adjusting the addition rate. After the addition was complete, the reaction was stirred at room temperature for 1 h. Sodium carbonate powder was added to the reaction mixture to adjust the pH to neutral, then 100 mL brine was added. The mixture was extracted with ethyl acetate twice, 2×80 mL, the organic phase was combined, washed with brine, dried with anhydrous sodium sulfate, filtered, and concentrated, 12.3 g of crude product was obtained.

After purification by vacuum distillation, 9.01 g of 8-methyldecanol was obtained, b.p. 112° C./0.15 mmHg. The overall yield of S2 and S3 was 65.4%.

S4 Preparation of 8-methyldecanal: 80 mL of dichloromethane and 20 mL of water were added to a three-neck flask equipped with a stirrer, a dropping funnel, and a thermometer. 0.125 g of 2, 2, 6, 6-tetramethylpiperidinyloxy, 0.068 g tetrabutylammonium hydrogen sulfate, and 77.5 g of sodium hypochlorite 10% solution were added. The reaction temperature was kept between 3-8° C., 13.78 g of 8-methyldecanol was added dropwise. After addition, the reaction was continued at 3-8° C. for 1-2 h, then 50 mL of saturated sodium sulfite solution was added to the reaction mixture. The organic phase was separated, and the water phase was extracted with 40 mL of dichloromethane. The organic phase were combined, washed with brine, dried with anhydrous sodium sulfate, filtered, and concentrated to provide 13.4 g of crude product.

After purification by vacuum distillation, 12.7 g of 8-methyldecanal was obtained with a yield of 93.2%, b.p. 108° C./0.15 mmHg.

Example 2

The example relates to a method for preparing 8-methyldecanal, which comprises the following steps:

S1 Protection of the hydroxyl group of 6-chloro-1-hexanol: 100 mL of dichloromethane was added to a three-neck flask equipped with a stirrer, a dropping funnel and a thermometer. 0.2 g of p-toluenesulfonic acid and 20.0 g of 6-chloro-1-hexanol were added to the flask under nitrogen and the temperature of the reaction system was kept between 0-10° C. Then 16.8 g of 3, 4-dihydropyran was added through the dropping funnel. The reaction was exothermic, the temperature of the reaction system was kept between 0-10° C. by adjusting the addition rate. After the addition was complete, the reaction was continued at low temperature for 1-2 h, then 40 mL of saturated sodium bicarbonate solution was added. The mixture was stirred for 10-15 min, 20 mL of water was added. The organic phase was separated, washed with 50 mL of saturated sodium chloride solution, dried with anhydrous sodium sulfate, filtered, and concentrated to obtain 35.06 g of crude product.

After short-range vacuum distillation, 29.42 g of 6-chloro-hexyl tetrahydropyran ether was obtained, b.p. 145° C./0.16 mmHg, with a yield of 92.1%.

S2 Preparation of 8-methyl-decyl tetrahydropyran ether: 100 mL of anhydrous tetrahydrofuran was added to a three-neck flask equipped with a stirrer, a dropping funnel and a thermometer. Under nitrogen atmosphere, 4.4 g of magnesium turnings, 1.0 g of iodine, and 1.6 g of 1, 2-dibromoethane were added to the flask. The reaction temperature was kept below 60° C., and 22.0 g of 6-chloro-1-hexanol tetrahydropyran ether was added dropwise. Because the reaction was exothermic, the reaction temperature was kept below 60° C. by adjusting the addition rate. After the addition was complete, the reaction mixture was gently refluxed for 2 hours, while the solution changed from yellow color to clear and to black, and most of the magnesium turnings disappeared. Then system temperature was lowered to 35-45° C., 0.72 g of cuprous bromide was added in one portion. 15.1 g of 1-bromo-2-methyl-butane was added dropwise. After addition was complete, the reaction system was heated to gently refluxing, and continued refluxing for 5-8 h. Afterwards, the mixture was cooled down to room temperature, 200 mL of saturated ammonium chloride solution, and 200 mL of ethyl acetate were added to the mixture. The organic phase was separated, washed with brine, dried with anhydrous sodium sulfate, filtered, and concentrated. 23.1 g of crude 8-methyl decyl tetrahydropyran ether was obtained. The crude product does not need to be purified and can be directly used in the next hydroxyl deprotection step.

S3 Deprotection of 8-methyl-decyl tetrahydropyran ether: 100 mL of methanol was added to a three-neck flask equipped with a stirrer, a dropping funnel, and a thermometer. 23.1 g of crude 8-methyl decyl tetrahydropyran ether was added, then 40 mL of 2M hydrochloric acid solution was added dropwise. Because the reaction was exothermic, the reaction temperature was kept below 40° C. by adjusting the addition rate. After the addition was complete, the reaction was stirred at room temperature for 1 h. Sodium carbonate powder was added to the reaction mixture to adjust the pH to neutral, then 100 mL brine was added. The mixture was extracted with ethyl acetate twice, 2×100 mL, the organic phase was combined, washed with brine, dried with anhydrous sodium sulfate, filtered, and concentrated, 15.1 g of crude product was obtained.

After purification by vacuum distillation, 11.4 g of 8-methyldecanol was obtained, b.p. 112° C./0.15 mmHg. The overall yield of S2 and S3 was 66.3%.

S4 Preparation of 8-methyldecanal: 100 mL of dichloromethane and 20 mL of water were added to a three-neck flask equipped with a stirrer, a dropping funnel, and a thermometer. 0.19 g of 2, 2, 6, 6-tetramethylpiperidinyloxy, 0.17 g tetrabutylammonium hydrogen sulfate, and 95.6 g of sodium hypochlorite 10% solution were added. The reaction temperature was kept between 3-8° C., 17.03 g of 8-methyldecanol was added dropwise. After addition, the reaction was continued at 3-8° C. for 1-2 h, then 50 mL of saturated sodium sulfite solution was added to the reaction mixture. The organic phase was separated, and the water phase was extracted with 50 mL of dichloromethane. The organic phase were combined, washed with brine, dried with anhydrous sodium sulfate, filtered, and concentrated to provide 16.8 g of crude product.

After purification by vacuum distillation, 16.1 g of 8-methyldecanal was obtained with a yield of 95.1%, b.p. 108° C./0.15 mmHg.

Example 3

The example relates to a method for preparing 8-methyldecanal, which comprises the following steps:

S1 Protection of the hydroxyl group of 6-chloro-1-hexanol: 120 mL of dichloromethane was added to a three-neck flask equipped with a stirrer, a dropping funnel and a thermometer. 0.25 g of p-toluenesulfonic acid and 24.66 g of 6-chloro-1-hexanol were added to the flask under nitrogen and the temperature of the reaction system was kept between 0-10° C. Then 25.2 g of 3, 4-dihydropyran was added through the dropping funnel. The reaction was exothermic, the temperature of the reaction system was kept between 0-10° C. by adjusting the addition rate. After the addition was complete, the reaction was continued at low temperature for 1-2 h, then 60 mL of saturated sodium bicarbonate solution was added. The mixture was stirred for 10-15 min, 40 mL of water was added. The organic phase was separated, washed with 80 mL of saturated sodium chloride solution, dried with anhydrous sodium sulfate, filtered, and concentrated to obtain 42.5 g of crude product.

After short-range vacuum distillation, 36.5 g of 6-chlorohexyl tetrahydropyran ether was obtained, b.p. 145° C./0.16 mmHg, with a yield of 91.9%.

S2 Preparation of 8-methyl-decyl tetrahydropyran ether: 120 mL of anhydrous tetrahydrofuran was added to a three-neck flask equipped with a stirrer, a dropping funnel and a thermometer. Under nitrogen atmosphere, 4.8 g of magnesium turnings, 1.6 g of iodine, and 2.26 g of 1, 2-dibromoethane were added to the flask. The reaction temperature was kept below 60° C., and 26.5 g of 6-chloro-1-hexanol tetrahydropyran ether was added dropwise. Because the reaction was exothermic, the reaction temperature was kept below 60° C. by adjusting the addition rate. After the addition was complete, the reaction mixture was gently refluxed for 2 hours, while the solution changed from yellow color to clear and to black, and most of the magnesium turnings disappeared. Then system temperature was lowered to 35-45° C., 1.14 g of cuprous bromide was added in one portion. 18.12 g of 1-bromo-2-methyl-butane was added dropwise. After addition was complete, the reaction system was heated to gently refluxing, and continued refluxing for 5-8 h. Afterwards, the mixture was cooled down to room temperature, 250 mL of saturated ammonium chloride solution, and 200 mL of ethyl acetate were added to the mixture. The organic phase was separated, washed with brine, dried with anhydrous sodium sulfate, filtered, and concentrated. 28.5 g of crude 8-methyl decyl tetrahydropyran ether was obtained. The crude product does not need to be purified and can be directly used in the next hydroxyl deprotection step.

S3 Deprotection of 8-methyl-decyl tetrahydropyran ether: 120 mL of methanol was added to a three-neck flask equipped with a stirrer, a dropping funnel, and a thermometer. 28.5 g of crude 8-methyl decyl tetrahydropyran ether was added, then 60 mL of 2M hydrochloric acid solution was added dropwise. Because the reaction was exothermic, the reaction temperature was kept below 40° C. by adjusting the addition rate. After the addition was complete, the reaction was stirred at room temperature for 1 h. Sodium carbonate powder was added to the reaction mixture to adjust the pH to neutral, then 150 mL brine was added. The mixture was extracted with ethyl acetate twice, 2×150 mL, the organic phase was combined, washed with brine, dried with anhydrous sodium sulfate, filtered, and concentrated, 18.5 g of crude product was obtained.

After purification by vacuum distillation, 13.3 g of 8-methyldecanol was obtained, b.p. 112° C./0.15 mmHg. The overall yield of S2 and S3 was 64.8%.

S4 Preparation of 8-methyldecanal: 120 mL of dichloromethane and 20 mL of water were added to a three-neck flask equipped with a stirrer, a dropping funnel, and a thermometer. 0.192 g of 2, 2, 6, 6-tetramethylpiperidinyloxy, 0.27 g tetrabutylammonium hydrogen sulfate, and 114.5 g of sodium hypochlorite 10% solution were added. The reaction temperature was kept between 3-8° C., 20.4 g of 8-methyldecanol was added dropwise. After addition, the reaction was continued at 3-8° C. for 1-2 h, then 80 mL of saturated sodium sulfite solution was added to the reaction mixture. The organic phase was separated, and the water phase was extracted with 80 mL of dichloromethane. The organic phase were combined, washed with brine, dried with anhydrous sodium sulfate, filtered, and concentrated to provide 19.5 g of crude product.

After purification by vacuum distillation, 18.7 g of 8-methyldecanal was obtained with a yield of 93.2%, b.p. 108° C./0.15 mmHg.

The invention claimed is:

1. A method of preparing 8-methyldecanal, comprising the following steps:
   step 1, mixing 6-chloro-1-hexanol and dihydropyran and adding an acidic catalyst into a mixture of 6-chloro-1-hexanol and dihydropyran to produce 6-chloro-hexyl tetrahydropyran ether;
   step 2, reacting the 6-chloro-hexyl tetrahydropyran ether obtained in step 1 with magnesium turnings to form a Grignard reagent, and then reacting with 1-bromo-2-methyl-butane to obtain the intermediate 8-methyl-decyl tetrahydropyran ether;
   step 3 under acidic conditions, deprotecting 8-methyl-decyl tetrahydropyran ether obtained in step 2 to obtain 8-methyl-1-decyl alcohol; and
   step 4, oxidizing the 8-methyl-1-decyl alcohol obtained in step 3 with 2, 2, 6, 6-tetramethylpiperidinyloxy to obtain 8 methyldecanal.

2. The method of preparing 8-methyldecanal according to claim 1, wherein the step 1 comprises the following steps:
   dissolving para-toluene sulfonic acid and 6-chloro-1-hexanol in dichloromethane under nitrogen atmosphere, while maintaining the temperature of the reaction system at 0-10° C.;
   adding dihydropyran dropwise, and stirring the reaction mixture for 1-2 h;
   neutralizing the reaction mixture with saturated sodium bicarbonate solution;
   separating, washing, drying, filtering, concentrating, and distilling the reaction mixture under vacuum to provide the 6-chloro-hexyl tetrahydropyran ether.

3. The method of preparing 8-methyldecanal according to claim 2, wherein the molar ratio of the amount of para-toluene sulfonic acid, the 6-chloro-1-hexanol, and the dihydropyran is (0.05-0.15):1:(1-2).

4. The method of preparing 8-methyldecanal according to claim 2, wherein the amount of the dichloromethane is 4-6 times the amount of the 6-chloro-1-hexanol.

5. The method of preparing 8-methyldecanal according to claim 1, wherein the step 2 comprises the following steps:
   mixing magnesium turnings, iodine, and 1, 2-dibromoethane in anhydrous tetrahydrofuran, then slowly adding 6-chloro-hexyl tetrahydropyran ether, and maintaining the reaction temperature under 60° C.;

after the addition was complete, stirring the reaction mixture for 2-3 h; adding cuprous bromide to the reaction mixture while the system temperature was 35-45° C.;

adding 1-bromo-2-methyl-butane dropwise;

after the addition, stirring the reaction mixture for 5-8 h;

during the work up, washing the organic phase with saturated ammonium chloride solution washing, drying, filtering, concentrating, distilling the crude mixture under vacuum to obtain the 8-methyl-decyl tetrahydropyran ether.

6. The preparation method of 8-methyldecanal according to claim 5, wherein the molar ratio of the magnesium turnings, the 1, 2-dibromoethane, the 6-chloro-hexyl tetrahydropyran ether, the cuprous bromide, and the 1-bromo-2-methyl-butane is (1.2-1.5):(0.1-0.2):1:(0.1-0.2):(1.5-0.2): (1.5-2);

the amount of iodine is 0.03-0.08 times the mass of the 6-chloro-hexyl tetrahydropyran ether, the volume amount of the tetrahydrofuran is 4-6 times that of the 6-chloro-hexyl tetrahydropyran ether, and the volume amount of the organic solvent is 8-12 times that of the 6-chloro-hexyl tetrahydropyran ether.

7. The preparation method of 8-methyl decanal according to claim 1, wherein the step 3 comprises the following steps:

dissolving crude 8-methyl decyl tetrahydropyran ether in methanol, then adding excessive of acid solution slowly to the reaction mixture, and maintaining the reaction temperature below 40° C.;

when the reaction was complete, adjusting the system pH to neutral, and adding brine;

extracting the mixture with an organic solvent, then washing, drying, filtering, concentrating, and distilling the organic phase to obtain the 8-methyldecanol.

8. The method for preparing 8-methyldecanal according to claim 7, wherein the volume of the methanol used is 4-6 of the mass amount of the crude 8-methyl-decyl tetrahydropyran ether;

the volume and dosage of the organic solvent is 8-12 times the mass and dosage of the crude 8-methyl-decyl tetrahydropyran ether, the acidic solution is selected from hydrochloric acid, sulfuric acid, acetic acid, and nitric acid.

9. The preparation method of 8-methyldecanal according to claim 1, wherein the step 4 comprises the following steps:

mixing 2, 2, 6, 6-tetramethylpiperidinyloxy, tetrabutylammonium hydrogen sulfate, and sodium hypochlorite solution in methylene chloride and water, and maintaining the temperature of the reaction system between 3-8° C., then adding 8-methyldecanol dropwise to the reaction system;

after addition, stirring the reaction mixture for 1-2 h, then adding saturated sodium sulfite solution;

separating the organic phase, extracting the aqueous phase with an organic solvent, and then washing, drying, filtering, concentrating, and distilling the combined organic phase under vacuum to obtain the 8-methyldecyl alcohol.

10. The method for preparing 8-methyldecanal according to claim 9, wherein the molar ratio of 2, 2, 6, 6-tetramethylpiperidinyloxy, tetrabutylammonium hydrogen sulfate, sodium hypochlorite, and 8-methyldecanol is (0.08~0.12): (0.02~0.08):(1.0~1.5):1; the volume ratio of methylene chloride to water is (4-6):1, the volume of methylene chloride used is 4-6 times of that of 8-methyldecanol, the volume of other organic solvent used is 2 to 3 times of that of 8-methyldecanol.

* * * * *